(12) United States Patent
Ogorzaly et al.

(10) Patent No.: US 12,344,844 B2
(45) Date of Patent: Jul. 1, 2025

(54) DNA APTAMERS SPECIFIC OF ADENOVIRUS TYPES

(71) Applicant: LUXEMBOURG INSTITUTE OF SCIENCE AND TECHNOLOGY (LIST), Esch-sur-Alzette (LU)

(72) Inventors: Leslie Ogorzaly, Ay-sur-Moselle (FR); Samuel Jourdan, Aubange-Battincourt (BE); Catherine Mulholland, Antrim (IE)

(73) Assignee: LUXEMBOURG INSTITUTE OF SCIENCE AND TECHNOLOGY (List), Esch/Alzette (LU)

( * ) Notice: Subject to any disclaimer, the term of this patent is extended or adjusted under 35 U.S.C. 154(b) by 1017 days.

(21) Appl. No.: 17/416,735

(22) PCT Filed: Dec. 2, 2019

(86) PCT No.: PCT/EP2019/083284
§ 371 (c)(1),
(2) Date: Jun. 21, 2021

(87) PCT Pub. No.: WO2020/126435
PCT Pub. Date: Jun. 25, 2020

(65) Prior Publication Data
US 2022/0073920 A1 Mar. 10, 2022

(30) Foreign Application Priority Data
Dec. 21, 2018 (LU) .......................... 101073

(51) Int. Cl.
*C12N 15/115* (2010.01)
*G01N 33/53* (2006.01)

(52) U.S. Cl.
CPC ....... *C12N 15/115* (2013.01); *G01N 33/5308* (2013.01); *C12N 2310/16* (2013.01); *G01N 2333/075* (2013.01)

(58) Field of Classification Search
CPC .............. C12N 15/115; C12N 2310/16; G01N 2333/075
See application file for complete search history.

(56) References Cited

U.S. PATENT DOCUMENTS 5,876,930 A * 3/1999 Livak .................. C12Q 1/6818
536/26.6
9,562,900 B2 2/2017 Bruno
2017/0114420 A1 4/2017 Jaykus et al.

FOREIGN PATENT DOCUMENTS

EP 2613147 B1 3/2015
EP 2859121 B1 4/2015
WO WO-0192512 A2 * 12/2001 ........... C12N 15/102
WO WO-2010115833 A1 * 10/2010 ........... C12Q 1/6886

OTHER PUBLICATIONS

Sarantis et al., (J. Clin. Microbiol 42(9): 3963-3969, 2004) (Year: 2004).*
Hasegawa et al., (Molecules 2016, 21, 421, 15, pages) (Year: 2016).*
Enrique et al., Concentration of Enteric Adenovirus 40 From Tap, Sea and Waste Water, Water Research, Nov. 1995, vol. 29, No. 11, pp. 2554-2560, published by Elsevier Ltd.
Lee et al., Molecular Detection of Human Enteric Viruses in Urban Rivers in Korea, J Microbiol Biotechnol, Jul. 2008, vol. 6, pp. 1156-1163, published by National Library of Medicine.
Verheyen et al., Detection of Adenoviruses and Rotaviruses in Drinking Water Sources Used in Rural Areas of Benin, West Africa, Applied and Environmental Microbiology, May 2009, pp. 2798-2801, published by American Society for Microbiology.
Ogorzaly et al., Occurrence, Survival, and Persistence of Human Adenoviruses and F-Specific RNA Phages in Raw Groundwater, Applied and Microbiology, Dec. 2010, pp. 8019-8025, published by American Society for Microbiology.
Wyn-Jones et al., Surveillance of Adenoviruses and Noroviruses in European Recreational Waters, Water Research, Oct. 2010, pp. 1025-1038, published by Elsevier Ltd.
International Search Report for PCT/EP2019/083284 mailed Feb. 4, 2020.
Written Opinion for PCT/EP2019/083284 mailed Feb. 4, 2020.

* cited by examiner

*Primary Examiner* — Richard A Schnizer
(74) *Attorney, Agent, or Firm* — Scott T. Gray; Sandberg Phoenix & von Gontard, PC

(57) ABSTRACT

A single stranded nucleic acid aptamer able to specifically bind to at least one Adenovirus type, the aptamer comprising or consisting of one of sequences SEQ ID NO:1 to 3, or variants thereof having at least 50% sequence identity. Additionally, a composition comprising the aptamer. Furthermore, use of the aptamer, for detecting, capturing, concentrating and/or quantifying at least one Adenovirus type. Still further, in vitro methods for capturing, detecting and/or quantifying at least one Adenovirus type. Further yet, a kit for detecting, quantifying, capturing and/or concentrating at least one Adenovirus type.

13 Claims, 3 Drawing Sheets
Specification includes a Sequence Listing.

DNA APTAMERS SPECIFIC OF ADENOVIRUS TYPES

The present invention is the US national stage under 35 U.S.C. § 371 of International Application No. PCT/EP2019/083284 which was filed on Dec. 2, 2019, and which claims the priority of application LU 101073 filed on Dec. 21, 2018, the content of which (text, drawings and claims) are incorporated here by reference in its entirety.

FIELD

The invention is directed to aptamers specific of one or more Adenovirus types and their applications.

BACKGROUND

Enteric viruses (enteroviruses, noroviruses, adenoviruses and hepatitis A and E viruses among others) are present in faeces of infected persons in high concentrations and can be spread subsequently in the aquatic environment by the way of wastewater effluents. These viruses are mainly transmitted from person to person, or through contaminated food and drinking water, and bathing or recreational activities. Among these viruses, human adenoviruses (HAdV) are capable of causing many diseases, including gastroenteritis, conjunctivitis, myocarditis and pneumonia. Geographically, these viruses are distributed worldwide and commonly found in various water sources including river water, seawater or groundwater. In comparison to other enteric viruses (e.g. enteroviruses or noroviruses), they are usually more abundant (Lee and Kim, 2008; Verheyen et al., 2009; Wyn-Jones et al., 2011), found throughout the year and have noteworthy survival characteristics in water (Enriquez et al., 1995; Ogorzaly et al., 2010).

Adenoviruses (AdV) belong to the Adenoviridae family, a family of non-enveloped viruses, double stranded DNA genome. Depending on the analytical framework and on the kind of samples (clinical, food or environmental samples), different detection methods targeting either the viral genome or the capsid can be applied, each with its advantages and drawbacks. Molecular amplification methods, i.e. polymerase chain reaction (PCR) are commonly used in food and environmental settings, while immunological techniques such as enzyme linked immunosorbent assays (ELISA) using antibodies are the rule for clinical samples. Antigenic methods work properly on samples presenting a high virus concentration but it is not sensitive enough for environmental and food samples. Moreover, the binding capacity of antibodies can be affected by complex matrices of the sample. Hence, there is a need to develop alternative AdV diagnostic tools to complement the existing ones, and thus provide a rapid, sensitive and effective method which will allow the relevant authorities to reduce the risk of infection from enteric illnesses and other diseases and limit the spread of the virus.

Prior art patent document published US 2017/0114420 A1 discloses aptamers specifically binding to noroviruses. The aptamers are used for detecting the presence of noroviruses and for capturing and/or concentrating noroviruses from test samples. However, there is no disclosure of a solution for detecting, capturing Adenovirus.

Prior art patent document U.S. Pat. No. 9,562,900 B2 discloses aptamers that specifically target and bind to foodborne and waterborne pathogens bacteria or parasites, molds or other pathogenic fungi. This document does not disclose tools for analyzing (detection etc. . . . ) viruses and more particularly adenoviruses in samples such as food or water.

Prior art documents published EP 2 859 121 B1 and EP 2 613 147 B1 disclose methods, devices, reagents, and kits for the detection of one or more target molecules that may be present in a test sample, using aptamers. These documents do not disclose any tool for analyzing adenoviruses.

SUMMARY

The invention has for technical problem to provide rapid, sensitive and effective tools for Adenovirus-type analysis in samples. The invention has also for technical problem to provide a solution which is not expensive.

The invention is directed to a single stranded nucleic acid aptamer able to specifically bind to at least one Adenovirus type, the aptamer comprising or consisting of one of sequences SEQ ID NO:1 to 3, or variants thereof having at least 50% sequence identity.

The invention is also directed to a composition comprising at least one single stranded nucleic acid aptamer able to specifically bind to at least one Adenovirus type, the aptamer comprising or consisting of one of sequences SEQ ID NO:1 to 3 or variants thereof having at least 50% sequence identity and at least one Adenovirus type.

The invention is also directed to the use of a single stranded nucleic acid aptamer able to specifically bind to at least one Adenovirus type, the aptamer comprising or consisting of one of sequences SEQ ID NO:1 to 3 or variants thereof having at least 50% sequence identity, for detecting, capturing, quantifying and/or concentrating at least one Adenovirus type.

The invention is also directed to an in vitro method for capturing at least one Adenovirus type in a sample, comprising the step of contacting the sample with a single strand nucleic acid aptamer able to specifically bind to at least one Adenovirus type, the aptamer comprising or consisting of one of sequences SEQ ID NO:1 to 3 or variants thereof having at least 50% sequence identity.

The invention is also directed to an in vitro method for detecting and/or quantifying at least one Adenovirus type in a sample, comprising: performing the in vitro method for capturing according to the invention, quantifying, or detecting the presence or absence of bound aptamer to Adenovirus; deducing therefrom the amount or the presence or absence of Adenovirus in the sample.

According to an exemplary embodiment, quantifying, or detecting the presence or absence of bound aptamer to Adenovirus is performed via comparison with a control group.

According to an exemplary embodiment, wherein detecting the presence or absence of bound aptamer to Adenovirus in the sample is carried out by performing a PCR intended to amplify the aptamer, the PCR being performed with a set of two primers corresponding to sequences 5'-GTGCCAGC-TATGCCATTG-3' (SEQ ID NO: 4) and 5'-GCAGCAGAGATAGACGCTA-3' (SEQ ID NO: 5) and/or by Enzyme-Linked Aptamer Sorbent Assay.

According to an exemplary embodiment, wherein the at least one aptamer comprises a detectable label and detecting the presence or absence of bound aptamer to Adenovirus in the sample is carried out by detecting the label.

The invention is also directed to kits for detecting, quantifying, capturing and/or concentrating at least one Adenovirus type comprising at least one single strand of nucleic acid aptamer able to specifically bind to at least one Adenovirus type, the aptamer comprising or consisting of one of sequences SEQ ID NO:1 to 3 or variants thereof having at least 50% sequence identity.

According to an exemplary embodiment, an exemplary kit further comprises a support or a solution with at least one capture element of the at least one Adenovirus type and/or detection means.

According to an exemplary embodiment, the at least one capture element comprises one or more of the at least one aptamer.

According to an exemplary embodiment, the detection means comprises one or more of the aptamers with a detectable label linked thereto.

According to an exemplary embodiment, the detectable label is bound to the 5' or 3' end of the aptamer.

According to an exemplary embodiment, further comprising a set of two primers able to bound the at least one aptamer and corresponding to sequences 5'-GTGCCAGC-TATGCCATTG-3' (SEQ ID NO: 4) and 5'-GCAGCAGAGATAGACGCTA-3' (SEQ ID NO: 5) in order to amplify the aptamer bound to Adenovirus.

The invention is particularly interesting in that aptamers of the invention are specific of adenovirus types and are able to specifically bind different adenovirus types with high affinity. The aptamers can be used instead of commercial monoclonal antibodies. The aptamers show similar affinity to Adenovirus types as antibodies. The aptamers present a long-term stability. The aptamers are also advantageous is that they are of lower cost compared to antibodies and are easy to preserve. The methods and kit of the invention are easy to use and/or perform for quantifying, detecting, capturing and/or concentrating at least one Adenovirus types.

DRAWINGS

DETAILED DESCRIPTION

Production and Purification of Viral Stocks

Figure 1:
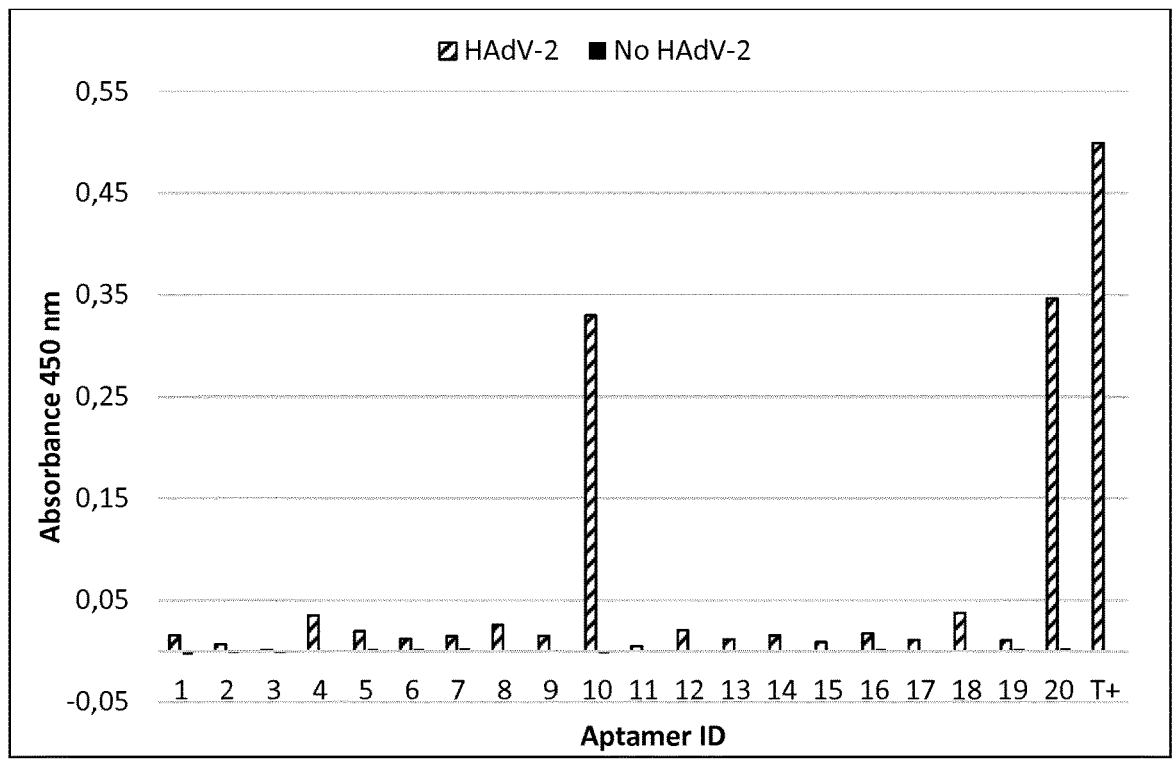
FIG. 1 represents direct ELISA results of HAdV-2 (approximatively $10^7$ MPN/well) incubated with twenty biotinylated candidate aptamers. All aptamers were used at the same concentration of 1 μM, in accordance with various embodiment of the invention.

HAdV-2 (Human adenovirus type 2) was chosen to perform the selection of aptamers. HAdV-2 was obtained from the Health Protection Agency culture collection (NCPV #213) and was propagated on the human embryonic kidney cell line 293A (Invitrogen). The cells were grown in Dulbecco's Modified Eagle Medium (D-MEM) containing high glucose concentration and Glutamax (Life Technologies), and supplemented with 1% of non-essential amino acids (Life Technologies) and 5% of non-heat inactivated foetal bovine serum (Life Technologies). HAdV-2 stock was prepared from infected 293A monolayers by freeze-thaw lysis followed by centrifugation (1200 rpm, 10 min, 4° C.) to remove cell debris. The viral suspension was then purified by cesium chloride equilibrium density gradient centrifugation. The purified AdV band was collected using a syringe and directly injected into a float-a-lyser dialysis device with a molecular weight cut off of 100 KDa (Spectrum Labs, USA). The dialysis device was placed in a 2 L container filled with Dubelcco's PBS (DPBS) (Gibco) with gentle rotation (50 rpm) at 4° C. The DPBS was changed after 2-4 hours, 6-8 hours and 12-14 hours. After the dialysis step, the viral suspension was collected and stored at 4° C. The quantification of the purified HAdV-2 stock was performed by a most probable number (MPN) assay using 293A cells (Ogorzaly et al. 2013).

Selection of Aptamers

A 65 base pair combinatorial DNA library (GTGCCAGC-TATGCCATTG (SEQ ID NO: 4)-N28-TAGCGTC-TATCTCTGCTGC (SEQ ID NO: 5)) with a constant forward and reverse regions and a 28 base-pair random region (N28) containing equimolar incorporation of A, T, C and G at each position was synthetized (Eurogentec). Before selection, 1 μM of the single-stranded DNA (ss DNA) pool in the selection buffer (herein referred to as SB) (consisting of DPBS (Gibco) supplemented with $MgCl_2$ (3 mM) and $NaCl_2$ (20 mM) at pH 7.4, and sterilised by autoclave followed by 0.2 μm membrane filtration), was heated to 95° C. to denature the DNA, then allowed to cool to room temperature for 30 min before incubating with the virus.

The following table 1 discloses the oligonucleotides used in the selection of aptamers for AdV.

TABLE 1

| Details of oligonucleotides | | Sequence 5-3' |
|---|---|---|
| D1-DNA Lib | D1 DNA aptamer library | GTGCCAGCTATGCCATTG (SEQ ID NO: 4)-N28-TAGCGTCTATCTCTGCTGC (SEQ ID NO: 5) |
| D1-Rev_Ph | D1 Phosphorylated Reverse | P-GCAGCAGAGATAGACGCTA (SEQ ID NO: 5) |
| D1-For | D1 Forward | GTGCCAGCTATGCCATTG (SEQ ID NO: 4) |
| D1-Rev | D1 Reverse | GCAGCAGAGATAGACGCTA (SEQ ID NO: 5) |

The target complex for SELEX was produced by immobilising purified HAdV-2 to the antibody-magnetic bead complex. Biotinylated monoclonal antibody 8C4 (HyTest, Finland) against AdV was conjugated to Streptavidin Dynabeads (ThermoFisher Scientific Aalst, Belgium) according to manufacturer's instructions. In brief, 100 μL of Streptavidin Dynabeads were aliquot and washed three times with wash buffer DPBS-T (PBS containing 0.005% Tween20). A three-fold excess of biotinylated monoclonal antibody 8C4 (30 μg) was bound to the Streptavidin Dynabeads by incubating for 1 hour at room temperature with mixing by pipetting every 5-10 minutes. The antibody-bead complex was separated by a magnet, washed three times with DPBS-T and eluted in 100 µL DPBS containing 0.05% bovine serum albumin (BSA, Sigma Darmstadt, Germany). One hundred µL of the purified HAdV-2 stock (corresponding to about $10^7$ MPN/mL) was mixed with 10 µL of antibody-bead complex suspended in 490 µL of SB and incubated 2 hours at room temperature. The target complex HAdV-2-antibody-bead was washed three-times with PBS supplemented by 0.1% BSA and finally re-suspended in 20 µL of DPBS.

SELEX was performed using the target complex (HAdV-2-antibody-bead) and negative SELEX was performed using the antibody-bead complex. Briefly 500 pmol/500 µL of the DNA library in selection buffer, was denatured by heating to 95° C. for 5 min and cooled to room temperature for 30 min. A negative selection was performed initially by incubating the DNA library with the antibody-bead complex for 45 min at room temperature, in-order to reduce the non-specific interactions of the DNA pool with the surface. The bound DNA was separated by magnet and the supernatant (recovered DNA library) was used directly for the first round of SELEX. The recovered DNA was added to 10 µL of target complex (corresponding to approximatively $10^7$ infectious viral particles/reaction) and incubated at room temperature for 30 min. The bound DNA sequences were recovered by magnetic capture and washed three times with DPBS-T to facilitate the removal of non-binders and/or poor binders. One hundred microliters of nuclease free water were added to the beads and the sample heated to 90° C. for 5 min to release the DNA. The ss-DNA was amplified by PCR using the constant forward primer and the phosphorylated reverse primer (Table 1). The PCR final volume was 50 µL of which 10 µL contained the DNA target. The reaction was performed on a Biometra T-Advanced 96SG System, (Germany) and the following conditions applied, 95° C. for 2 min followed by various cycles of 95° C. for 15 sec, 67° C. for 1 min, 72° C. for 30 sec and a final extension of 72° C. for 2 min. The PCR products were visualized on a 4% agarose gel stained with ethidium bromide. The PCR reaction was stopped when the 65 bp band appeared on the agarose gel. The double stranded DNA (ds DNA) was purified using spin columns (Nucleospin Gel and PCR clean-up system, Machery and Nagel). For the separation of the dsDNA, 1 µL of 1 U Lambda exonuclease (Thermo Scientific, UK) was incubated for 1 hour at 37° C. followed by ssDNA confirmation by 4% agarose gel electrophoresis. All selection rounds were carried out in the same manner, however with decreasing concentrations of HAdV-2 infectious particles and decreasing concentrations of DNA pool. The incubation time was also decreased between each round and the washing steps increased both in volume and in amount to increase the selection pressure on the process.

Identification of Aptamer Sequences

The ssDNA obtained from the $9^{th}$, $10^{th}$ and $11^{th}$ SELEX rounds were amplified by non-modified primers (D1 Forward and reverse in Table 1) at the same conditions described previously. The products were analyzed by 4% agarose gel stained with ethidium bromide and the 65 bp band excised and purified using the Purelink Quick gel extraction and PCR purification combo kit (Invitrogen). The purified products were cloned into a dual promoter PCR2.1 TOPO vector using the TOPO TA cloning kit (Invitrogen) according to manufacturer's instructions. In total, eighty-six white clones were selected for sequencing which was performed on the Sanger sequencer (Applied Biosystems).

Binding Affinity Study

A direct ELASA (Enzyme Linked Aptamer Sorbent Assay) method was undertaken to test the binding activity of each of the selected aptamers. Ninety-six-well polystyrene plates (Greiner) were coated with HAdV-2 particles at a concentration of $10^7$ MPN/mL (approximatively $10^6$ particles/well) and incubated at 37° C. for one hour. After washing five times with 300 µL of DPBS, wells were blocked with 300 µL of 3% BSA overnight at 4° C. After washing five times with 300 µL of DPBS, 1 µM of each biotinylated candidate aptamer diluted in 100 µL of selection buffer, were added to the wells and allowed to incubate for 1 hour at room temperature. Wells were washed twice with 300 µL of DPBS-T and twice with 300 µL of 1% BSA. One hundred microliters of streptavidin conjugated HRP (1/300, Thermo-Scientific) diluted in 1% BSA were added to each well and incubated for 30 min at room temperature in the dark. The plate was washed three times with 300 µL of DPBS and developed with 50 µL of TMB substrate solution (Thermo-Scientific) for 30 min in the dark at room temperature. Finally, 50 µL of 2M sulphuric acid was added to each well and the absorbance recorded at 450 nm (Tecan). Based on the results, the top three aptamers were chosen for further analysis.

The binding affinity of the selected aptamers were analyzed using the ELASA method described previously. HAdV-2 at a concentration of $10^7$ MPN/mL was coated onto 96 well polystyrene plates (Greiner) and reacted with varying concentrations (0-1000 nM) of the biotinylated aptamers 10 and 20. The plates were read at 450 nm and the OD values were inputted into SigmaPlot software and processed using one site saturation equation with non-specific binding to determine the Kd values.

FIG. 1 represents the results obtained for direct ELASA of purified HAdV-2 incubated with various biotinylated candidate aptamers at 1 µM.

Based on results from FIG. 1 aptamers 10, 18, 20 are the most promising candidates.

Figure 2:
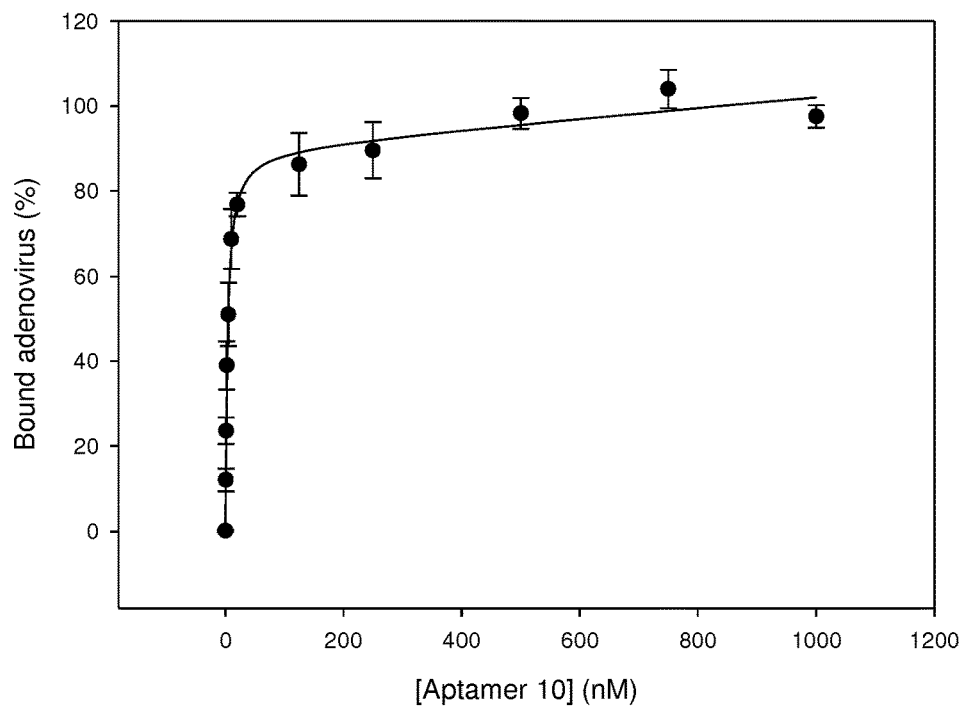
FIG. 2 shows the percentage of bound HAdV-2 according to the concentration of aptamer 10 comprising SEQ ID NO:1. The concentration of aptamer ranges from 0 to 1000 nM, in accordance with various embodiment of the invention.
Figure 3:
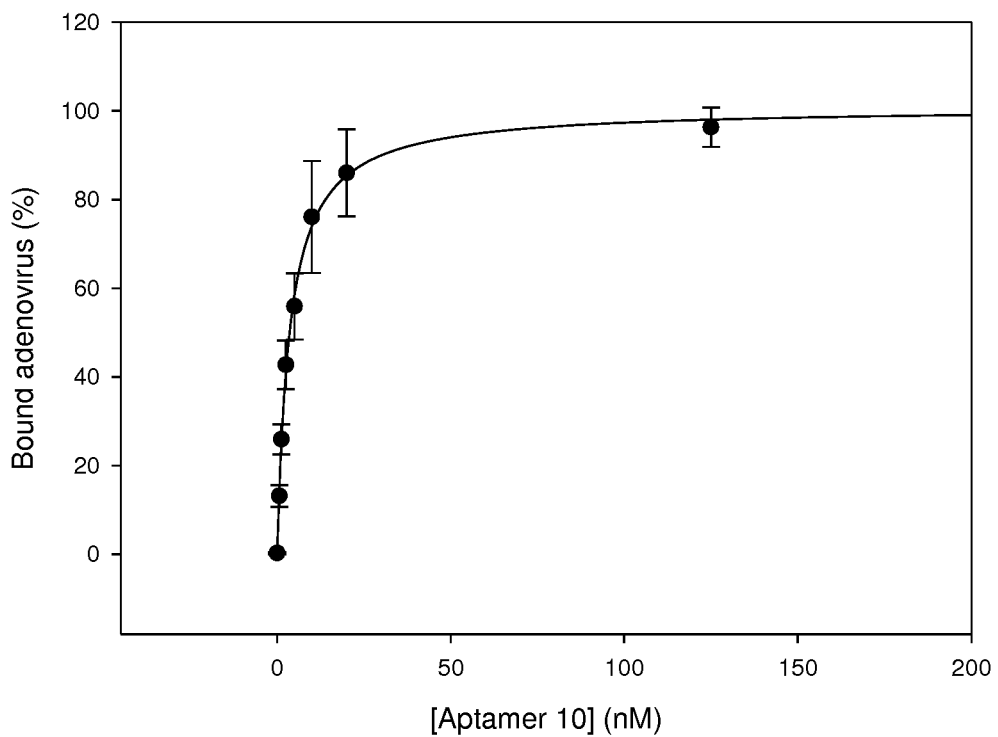
FIG. 3 is an enlarged view of FIG. 2 for concentration of aptamer ranging from 0 to 20 nM, in accordance with various embodiment of the invention.

FIGS. 2 and 3 represent the ELASA binding study of HAdV-2 and aptamer 10. The results indicate that aptamer 10 is able to specifically bind to HAdV-2 with high affinity. The Kd of the aptamer was calculated to be 3.6±0.7 nM. Each point is the mean of 6 independent experiments.

Figure 4:
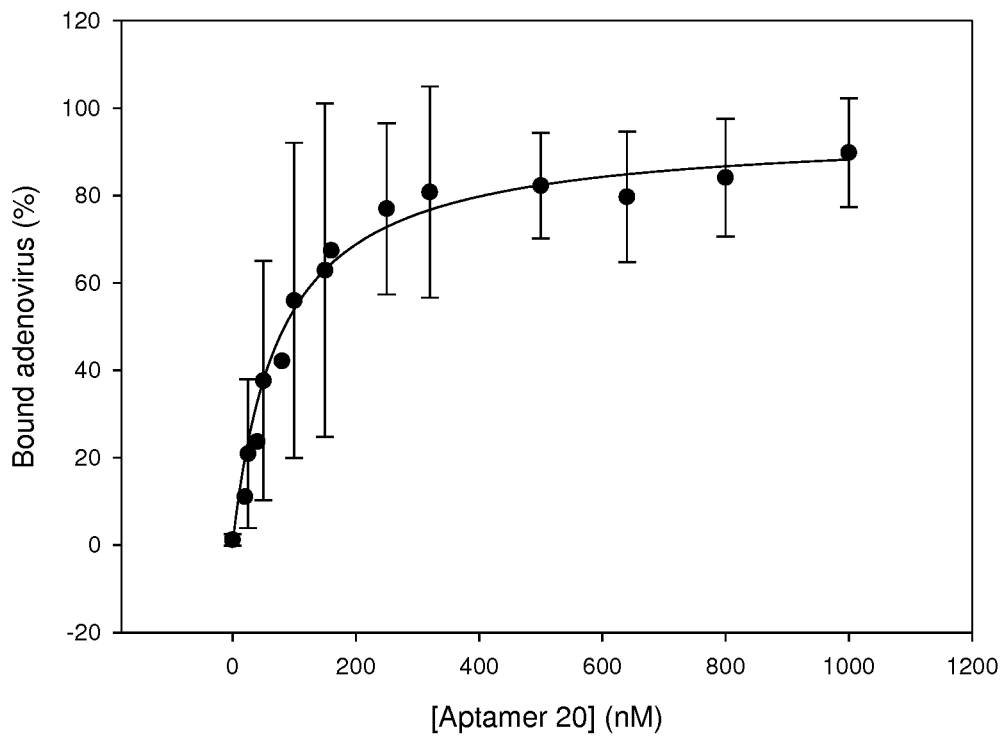
FIG. 4 shows the percentage of bound HAdV-2 according to the concentration of aptamer 20 comprising SEQ ID NO:3. The concentration of aptamer ranges from 0 to 1000 nM, in accordance with various embodiment of the invention.

FIG. 4 represents the ELASA binding study of HAdV-2 and aptamers 20. The results show that aptamer 20 is able to specifically bind to HAdV-2 with high affinity. The Kd value was estimated to be 75.9±68.6 nM. Each point is the mean of 7 independent experiments.

Specificity Study

The specificity of the aptamers 10 and 20 were analyzed by ELASA using various types of adenoviruses (Ovine adenovirus type 1 and bovine adenovirus type 9) and various types of other waterborne viruses (F-specific RNA bacteriophages strain MS2, GA, Qβ and SP). Target and non-target viruses were coated on the plate at the same initial concentration (approximatively 107 viral particles/well) and tested against an 80 nM concentration of aptamers 10 and 20, respectively, according to the ELASA protocol previously described.

Figure 5:
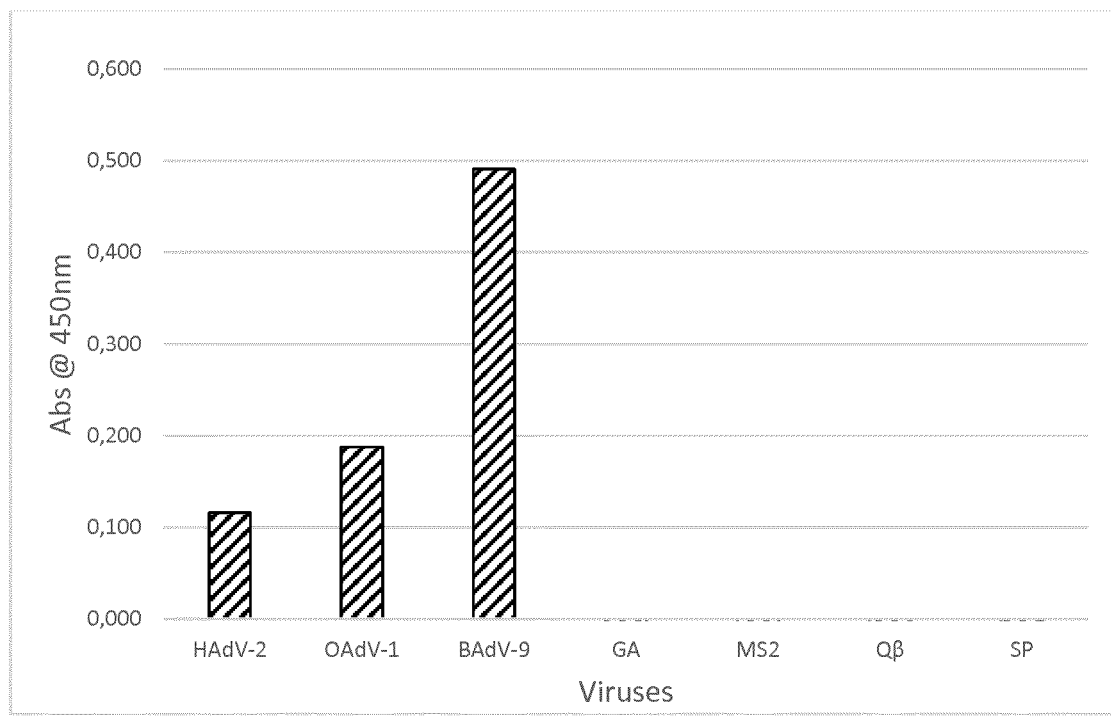
FIG. 5 shows the specificity of aptamer 10 for various viruses, in accordance with various embodiment of the invention.
Figure 6:
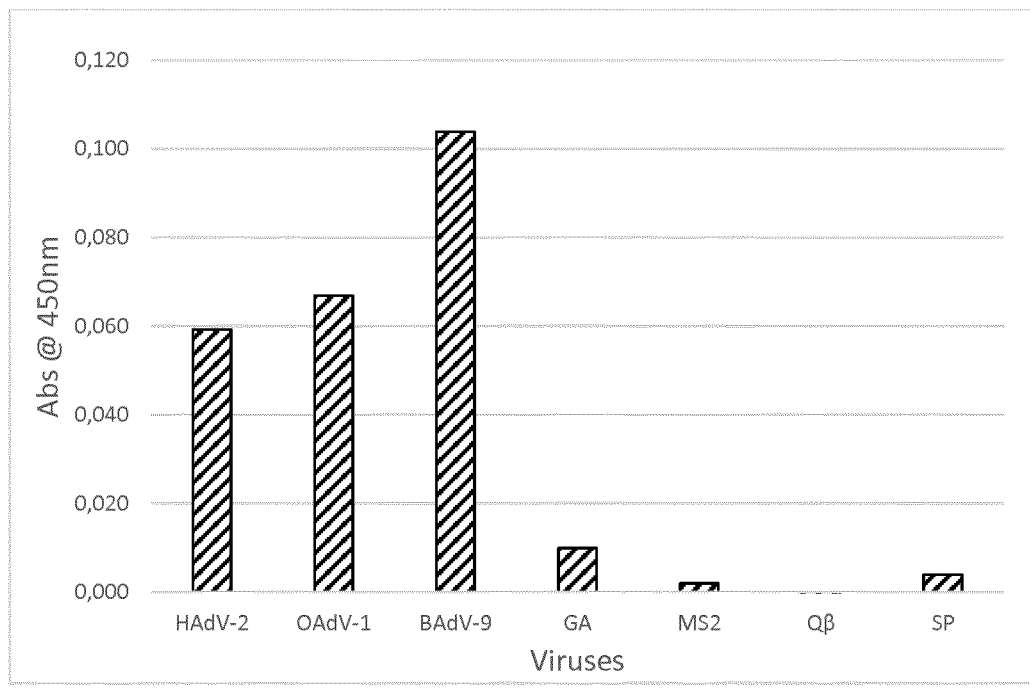
FIG. 6 shows the specificity of aptamer 20 for various viruses, in accordance with various embodiment of the invention.

The results are represented on FIGS. 5 and 6 and show that aptamers 10 and 20 are specific for adenovirus types. It produces a signal only for the adenoviruses and not for the other waterborne viruses.

Motif and Structure Analysis

Motif analysis was carried out by the online software program, MEME motif discovery tool. The predicted 2D folding of each aptamer was carried out by the online software program, MFOLD.

| Apt. ID | dG Value | SELEX Round | Random Region Sequence |
|---|---|---|---|
| 10 | 6.83 | 11 | 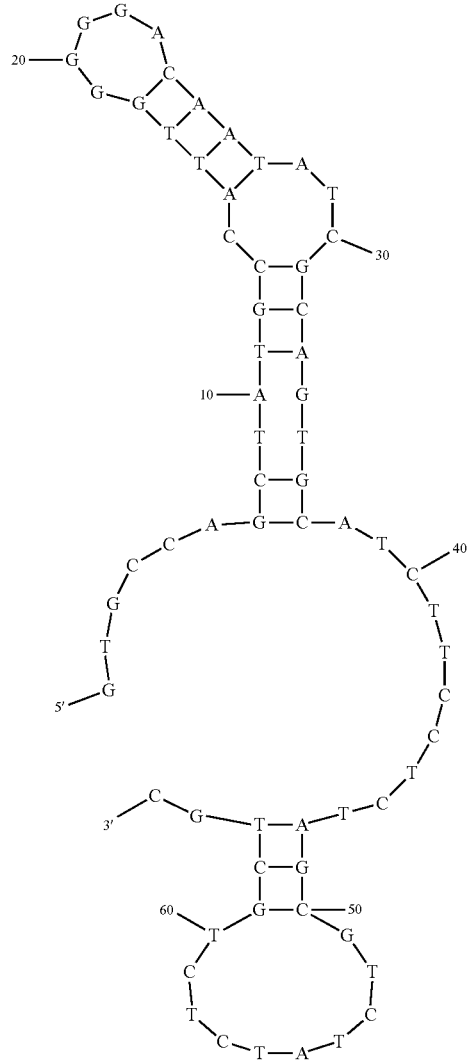 |
dG—6.83 PP12 Rd 11

-continued
| Apt. ID | dG Value | SELEX Round | Random Region Sequence |
|---|---|---|---|
| 18 | 7.72 | 11 | 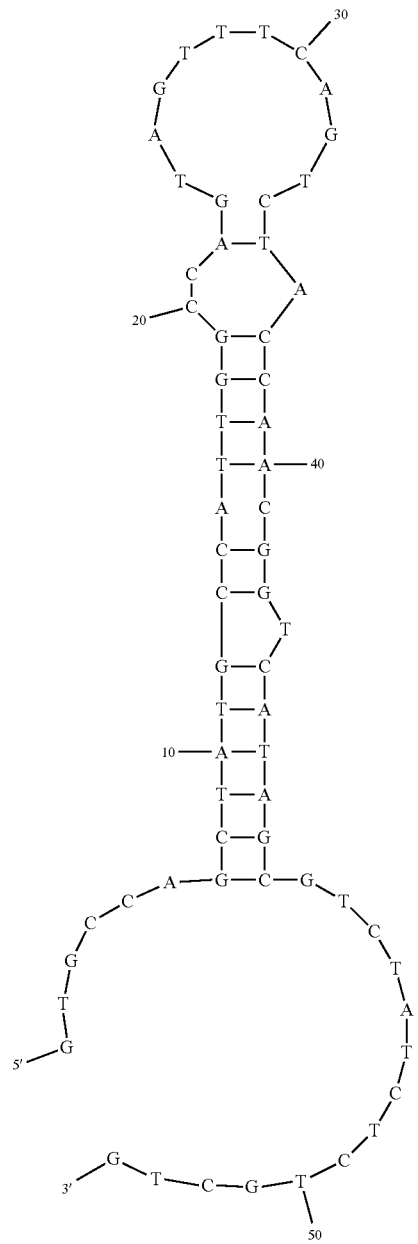 |
dG--7.72 Round 11 PP33

-continued

| Apt. ID | dG Value | SELEX Round | Random Region Sequence |
|---|---|---|---|
| 20 | −7.44 | 11 | (stem-loop structure diagram) | dG--7.44 Round 11 PP36

The following sequences have been identified:

SEQ ID NO: 1:
GTGCCAGCTATGCCATTGGGGGACAATATCGCAGTGCATCTTCCTCTAG
CGTCTATCTCTGCTGC.

SEQ ID NO: 2:
GTGCCAGCTATGCCATTGGCCAGTAGTTTCAGTCTACCAACGGTCATAG
CGTCTATCTCTGCTGC.

SEQ ID NO: 3:
GTGCCAGCTATGCCATTGGGCGGGTCGTCCAATTCGAGAGGTCCCCTAG
CGTCTATCTCTGCTGC.

Aptamers 10, 18 and 20 respectively comprise SEQ ID NO:1, SEQ ID NO:2, SEQ ID NO:3.

In accordance with various embodiments, the invention provides single stranded nucleic acid aptamer comprising or consisting of one of sequences SEQ ID NO:1 to 3, or variants thereof having at least 50% sequence identity. In various instances, the variants have at least 80% sequence identity, for example 90%.

The aptamers have at least one stem-loop structure.

In accordance with various embodiments, the invention also provides a composition comprising at least one single stranded nucleic acid aptamer comprising or consisting of one of sequences SEQ ID NO:1 to 3 or variants thereof having at least 50% sequence identity and at least one Adenovirus type.

The Adenovirus type can for example be a human or animal adenovirus.

In accordance with various embodiments, the invention also provides the use of a single stranded nucleic acid aptamer comprising or consisting of one of sequences SEQ ID NO:1 to 3 or variants thereof having at least 50% sequence identity, for detecting, capturing, quantifying and/or concentrating at least one Adenovirus type.

In accordance with various embodiments, the invention also provides an in vitro method for capturing at least one Adenovirus type in a sample, comprising the step of contacting the sample with a single strand nucleic acid aptamer comprising or consisting of one of sequences SEQ ID NO:1 to 3 or variants thereof having at least 50% sequence identity.

In accordance with various embodiments, the invention also provides an in vitro method for detecting and/or quantifying at least one Adenovirus type in a sample, comprising the steps of: performing the in vitro method for capturing as defined above, quantifying, or detecting the presence or absence of bound aptamer; and deducing therefrom the amount or the presence or absence of Adenovirus in the sample. Quantifying, or detecting the presence or absence of bound aptamer is performed via comparison with a control group. The method can comprise a step of removing unbound aptamer prior to the step of quantifying, or detecting the presence or absence of bound aptamer.

Detecting the presence or absence of bound aptamer in the sample is carried out by performing a PCR intended to amplify the bound aptamer, the PCR being performed with a set of two primers corresponding to sequences 5'-GTGCCAGCTATGCCATTG-3' (forward) (SEQ ID NO: 4) and 5'-GCAGCAGAGATAGACGCTA-3' (reverse) (SEQ ID NO: 5) and/or by Enzyme-Linked Aptamer Sorbent Assay (ELASA). Alternatively, the at least one aptamer comprises a detectable label, detecting the presence or absence of bound aptamer to Adenovirus in the sample is carried out by detecting the label.

In accordance with various embodiments, the invention also provides a kit for detecting, quantifying, capturing and/or concentrating at least one Adenovirus type comprising at least one single strand of nucleic acid comprising or consisting of one of sequences SEQ ID NO:1 to 3 or variants thereof having at least 50% sequence identity. According to an exemplary embodiment, the kit further comprises a support or a solution with at least one capture element of the at least one Adenovirus type and/or detection means. The support can be a solid support such as a polystyrene plate, magnetic beats or an extraction, chromatography or affinity column but are not limited to. According to an exemplary embodiment of the invention, the at least one capture element of the at least one Adenovirus type is at least one aptamer immobilized on the support or in solution.

The kit can also comprise detection means of bound aptamer with an adenovirus. According to an exemplary embodiment, the detection means comprises one or more of the aptamers with a detectable label linked thereto.

The detectable label may be a moiety, which may be detected by methods known in the art. For example, the detectable label may be an optical label, an electrochemical label, a radioisotope or a combination thereof. The detectable label may be attached to a specific base of the aptamer, a specific site of a specific structure such as a hairpin-loop structure of the aptamer, or a 3'-end or 5'-end of the aptamer. The optical label may be, for example, a fluorescent material. In addition, the optical label may be an enzyme, and such an enzyme may be used for enzyme-linked immunosorbent assay (ELISA). Other materials may be appropriately selected by one of ordinary skill in the art.

The kit further comprises a set of two primers able to bound the at least one aptamer and corresponding to sequences 5'-GTGCCAGCTATGCCATTG-3' (SEQ ID NO: 4) and 5'-GCAGCAGAGATAGACGCTA-3' (SEQ ID NO: 5) in order to amplify the aptamer bound to Adenovirus.

The kit may further include instructions for use. The kit may further comprise a positive control, for example an inactivated adenovirus particle and a negative control.

The samples can be clinical samples such as faeces, blood; environmental samples such as water, sediment and/or food samples but are not limited to.

The Computer Readable Form (CRF) of the sequence listing is identical to the "Sequence Listing" part of the disclosure.

---

The invention claimed is:

1. A single stranded nucleic acid aptamer able to bind specifically to at least one adenovirus type, said aptamer comprising at least one of sequences SEQ ID NO: 1 to 3.

2. A composition comprising at least one single stranded nucleic acid aptamer able to bind specifically to at least one adenovirus type, said aptamer comprising at least one of sequences SEQ ID NO: 1 to 3 and at least one adenovirus type.

3. An in vitro method for capturing at least one adenovirus type in a sample, comprising the step of contacting the sample with a single strand nucleic acid aptamer able to bind specifically to at least one adenovirus type, said aptamer comprising at least one of sequences SEQ ID NO: 1 to 3.

4. An in vitro method for at least one of detecting and quantifying at least one adenovirus type in a sample, comprising:
in vitro capturing of at least one adenovirus type in a sample by contacting the sample with a single strand nucleic acid aptamer able to bind specifically to at least one adenovirus type, said aptamer comprising at least one of sequences SEQ ID NO: 1 to 3;
one of quantifying or detecting one of the presence or absence of bound aptamer to adenovirus;
deducing therefrom one of the amount or the presence or the absence of adenovirus in the sample.

5. The in vitro method according to claim 4, wherein the one of quantifying or detecting the presence or absence of bound aptamer to adenovirus is performed via comparison with a control group.

6. The in vitro method according to claim 4, wherein detecting one of the presence or absence of bound aptamer to adenovirus in the sample is carried out by performing a PCR intended to amplify the aptamer, the PCR being performed with a set of two primers corresponding to at least one of sequences 5'-GTGCCAGCTATGCCATTG-3', being SEQ ID NO: 4, and 5'-GCAGCAGAGATAGACGCTA-3', being SEQ ID NO: 5, and by enzyme-linked aptamer sorbent assay.

7. The in vitro method according to claim 4, wherein the at least one aptamer comprises a detectable label and detecting the presence or absence of bound aptamer to adenovirus in the sample is carried out by detecting the label.

8. A kit for at least one of detecting, quantifying, capturing and concentrating at least one adenovirus type comprising at least one single strand of nucleic acid aptamer able to bind specifically to at least one adenovirus type, the aptamer comprising at least one of sequences SEQ ID NO: 1 to 3.

9. The kit according to claim 8 further comprising one of a support or a solution with at least one capture element for of the at least one adenovirus type and detection means.

10. The kit according to claim 9, wherein the at least one capture element comprises one or more of the at least one aptamer.

11. The kit according to claim 9, wherein the detection means comprises one or more of the aptamers with a detectable label linked thereto.

12. The kit according to claim 11, wherein the detectable label is bound to a 5' or 3' end of the one or more aptamers.

13. The kit according to claim 9, further comprising a set of two primers able to bound the at least one aptamer and corresponding to sequences 5'-GTGCCAGCTATGC-CATTG-3', being SEQ ID NO: 4, and 5'-GCAGCAGAGA-TAGACGCTA-3', being SEQ ID NO: 5, in order to amplify the aptamer bound to adenovirus.

* * * * *

SEQUENCE LISTING

```
<160> NUMBER OF SEQ ID NOS: 5

<210> SEQ ID NO 1
<211> LENGTH: 65
<212> TYPE: DNA
<213> ORGANISM: Artificial sequence
<220> FEATURE:
<223> OTHER INFORMATION: Aptamer specific of Adenoviruses

<400> SEQUENCE: 1
gtgccagcta tgccattggg ggacaatatc gcagtgcatc ttcctctagc gtctatctct    60
gctgc                                                                65

<210> SEQ ID NO 2
<211> LENGTH: 65
<212> TYPE: DNA
<213> ORGANISM: Artificial sequence
<220> FEATURE:
<223> OTHER INFORMATION: Aptamer specific of Adenoviruses

<400> SEQUENCE: 2
gtgccagcta tgccattggc cagtagtttc agtctaccaa cggtcatagc gtctatctct    60
gctgc                                                                65

<210> SEQ ID NO 3
<211> LENGTH: 65
<212> TYPE: DNA
<213> ORGANISM: Artificial sequence
<220> FEATURE:
<223> OTHER INFORMATION: Aptamer specific of Adenoviruses
```

```
<400> SEQUENCE: 3
gtgccagcta tgccattggg cgggtcgtcc aattcgagag gtcccctagc gtctatctct       60
gctgc                                                                   65

<210> SEQ ID NO 4
<211> LENGTH: 18
<212> TYPE: DNA
<213> ORGANISM: Artificial sequence
<220> FEATURE:
<223> OTHER INFORMATION: Oligonucleotide primer

<400> SEQUENCE: 4
gtgccagcta tgccattg                                                     18

<210> SEQ ID NO 5
<211> LENGTH: 19
<212> TYPE: DNA
<213> ORGANISM: Artificial sequence
<220> FEATURE:
<223> OTHER INFORMATION: Oligonucleotide primer

<400> SEQUENCE: 5
gcagcagaga tagacgcta                                                    19
```